United States Patent [19]

Sardina et al.

[11] Patent Number: 5,003,119
[45] Date of Patent: Mar. 26, 1991

[54] MANUFACTURE OF ALKYLBENZENES

[75] Inventors: Helion H. Sardina, Waldwick; Roger C. Johnson, Randolph; John E. Paustian, Whippany; Renata M. Cox, Wayne, all of N.J.

[73] Assignee: Lummus Crest, Inc., Bloomfield, N.J.

[21] Appl. No.: 478,749

[22] Filed: Feb. 12, 1990

Related U.S. Application Data

[63] Continuation of Ser. No. 191,351, May 9, 1988, abandoned.

[51] Int. Cl.[5] .......................... C07C 2/00; C07C 2/66; C07C 4/12
[52] U.S. Cl. .................................. 585/323; 585/449; 585/476; 585/484; 585/485; 585/486; 585/488
[58] Field of Search ............... 585/323, 449, 476, 484, 585/485, 486, 488

[56] References Cited

U.S. PATENT DOCUMENTS

| | | | |
|---|---|---|---|
| 3,062,903 | 11/1962 | Odioso et al. | 585/476 |
| 3,373,217 | 3/1968 | Engelbrecht et al. | 525/476 |
| 3,639,495 | 2/1972 | Brewer et al. | 585/476 |
| 3,668,264 | 6/1972 | Alley . | |
| 3,751,504 | 8/1973 | Keown et al. | 585/449 |
| 3,929,672 | 12/1975 | Ward . | |
| 4,009,217 | 2/1977 | Uitti | 585/323 |
| 4,107,224 | 8/1978 | Dwyer | 585/449 |
| 4,111,825 | 9/1978 | Schulz et al. | 585/450 |
| 4,169,111 | 9/1979 | Wight . | |
| 4,179,473 | 12/1979 | Cox | 585/323 |
| 4,185,040 | 1/1980 | Ward et al. . | |
| 4,341,913 | 7/1982 | Calcagno et al. | 585/449 |
| 4,343,957 | 8/1982 | Sartorio et al. | 585/449 |
| 4,347,393 | 8/1982 | Miki | 585/323 |
| 4,593,136 | 6/1986 | Kaeding et al. | 585/486 |
| 4,599,470 | 7/1986 | Gregory et al. | 585/323 |
| 4,691,068 | 9/1987 | Resh | 585/456 |

Primary Examiner—Curtis R. Davis
Attorney, Agent, or Firm—Elliot M. Olstein; Raymond J. Lillie

[57] ABSTRACT

A process for the manufacture of alkylbenzenes wherein a feed of fresh and recycle benzene and fresh olefin are reacted in the presence of an alkylation catalyst in an alkylator having at least two reaction stages wherein each stage is adiabatic. Essentially all of the olefin is completely reacted in each stage of the alkylator. Fresh olefin is fed into each stage of the alkylator. Preferred alkylbenzenes which are produced by this process are ethylbenzene and cumene.

19 Claims, 4 Drawing Sheets

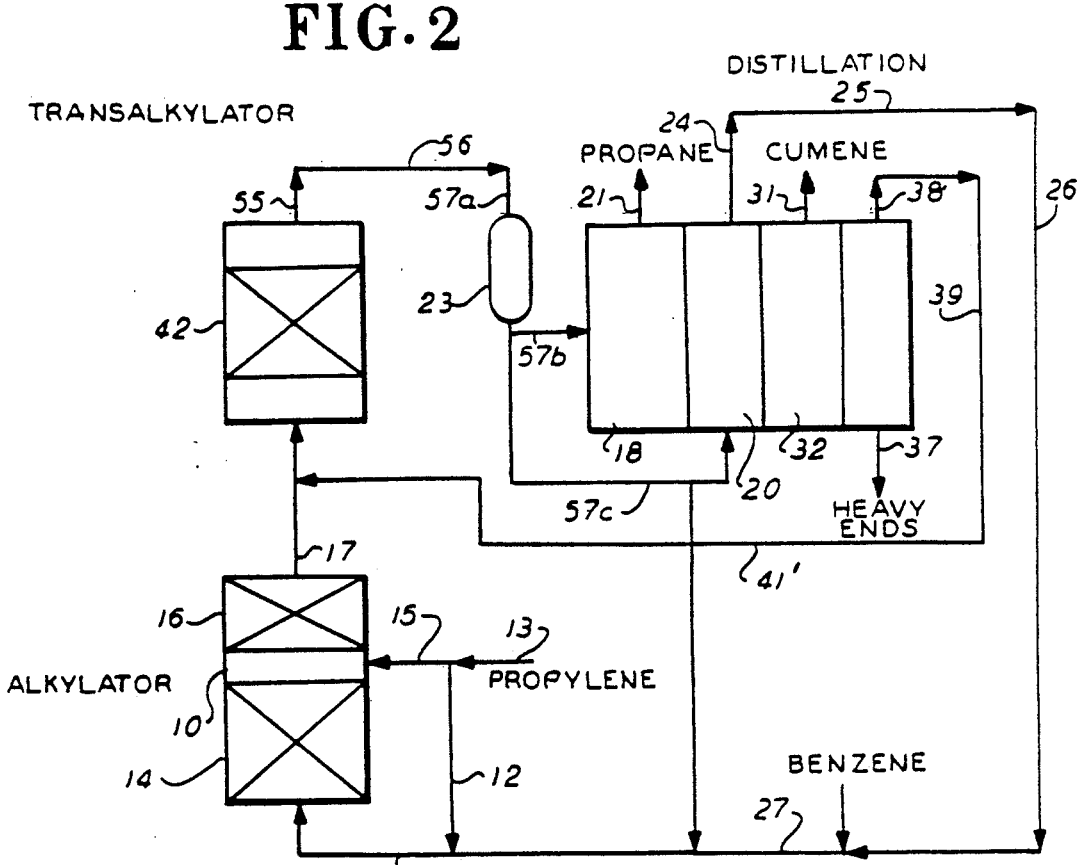
FIG. 2
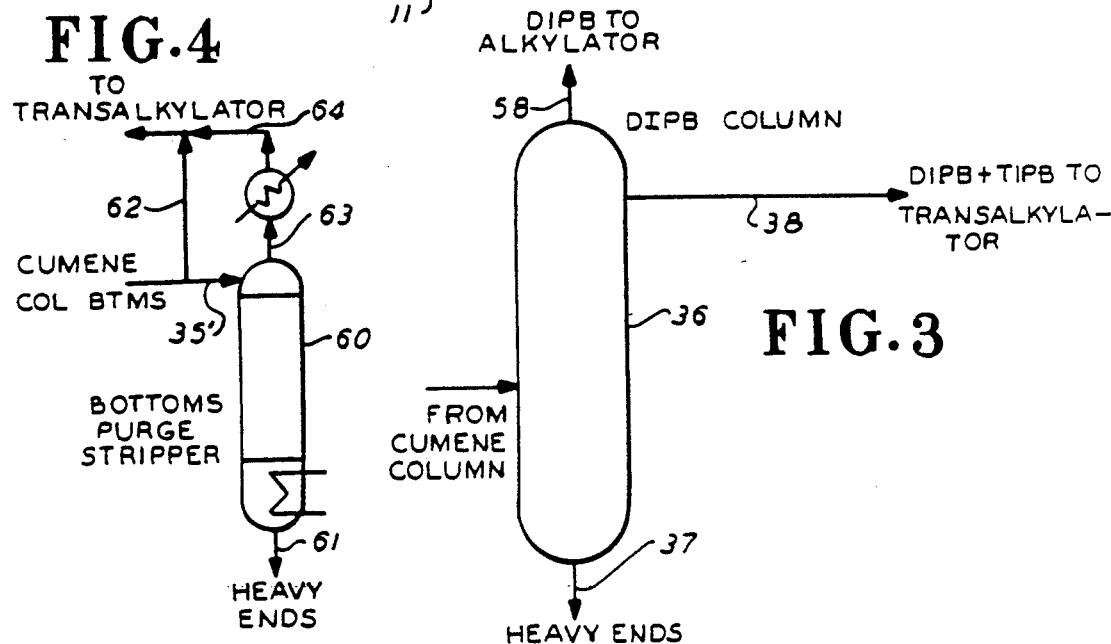
FIG. 4
FIG. 3

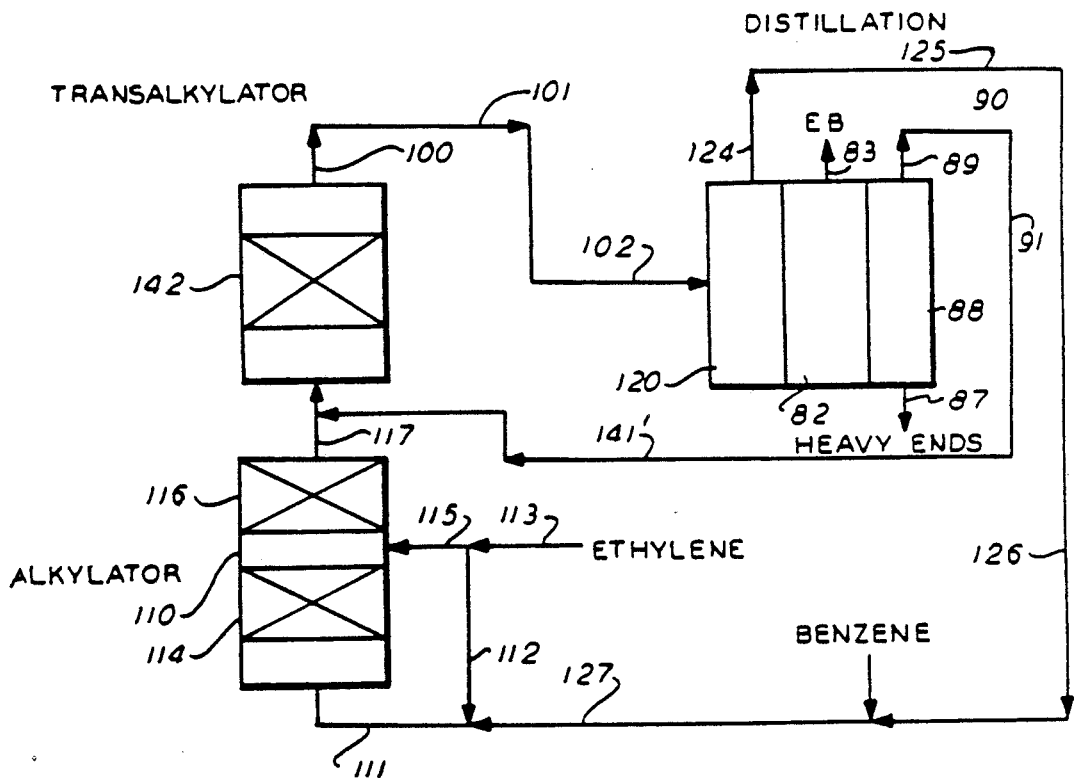
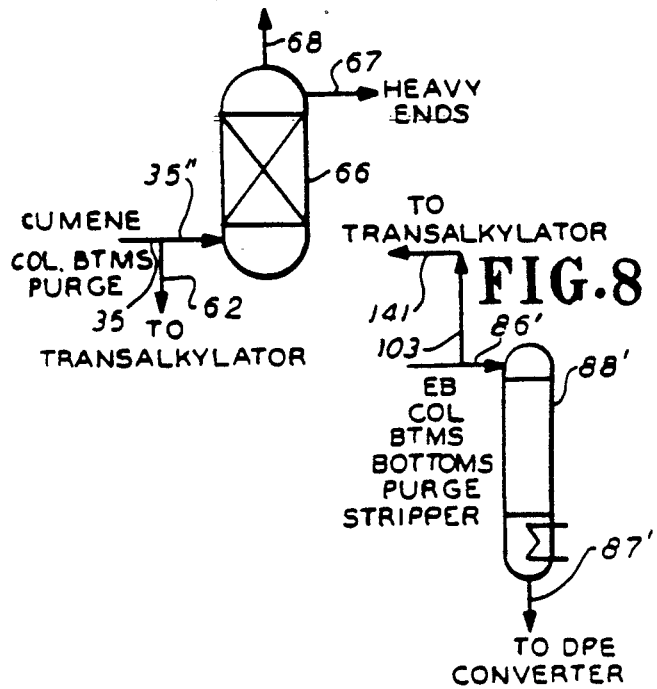
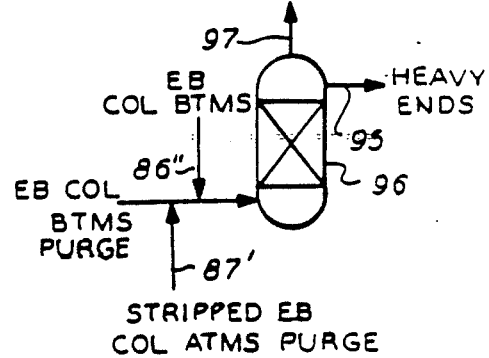

MANUFACTURE OF ALKYLBENZENES

This application is a continuation of application Ser. No. 07/191,351, filed May 9, 1988 and now abandoned.

This invention relates to the manufacture of alkylbenzenes by reacting benzene and olefin in the presence of an alkylation catalyst. More particularly, this invention relates to the manufacture of ethylbenzene and cumene by reacting benzene and ethylene or propylene in a staged alkylation reactor in the presence of an alkylation catalyst.

It has been known in the prior art to manufacture alkylbenzenes by reacting olefins and benzenes in the presence of an alkylation catalyst e.g., a zeolite catalyst. In a typical process, an olefin and benzene are fed through the inlet of an alkylation reactor which contains an alkylation catalyst. The effluent is introduced into a separation and recovery section to recover benzene, the desired alkylbenzene product (usually monoalkylbenzene), polyalkylbenzenes, so-called heavy ends, in particular diphenyl alkane. Polyalkylbenzenes may be directed to a transalkylator to be converted into more desirable monoalkylbenzene. Benzene may be sent to a transalkylator or recycled to the alkylator to be converted to alkylbenzenes.

In accordance with one embodiment of the present invention, benzene is alkylated in the presence of an alkylation catalyst by introducing a mixture of fresh and recycle benzene into an alkylator having at least two reaction stages, with fresh feed olefin being introduced into each stage of said alkylator. The temperature rise in each stage of the alkylator is preferably no more than 100° F., more preferably no more than 75° F. In a preferred embodiment, each of the reaction stages is adiabatic, i.e., no external heating or cooling is supplied to the stages of the alkylator and alkylation process. In another embodiment, the temperature at the outlet of each of said reaction stages does not exceed the outlet temperature of the preceding reaction stage. Most preferably, the temperature conditions in each stage remain the same. Preferably, the olefin is essentially completely reacted with the benzene in each reaction stage of the alkylator. Essentially all of the benzene required for the alkylation is introduced into the first alkylation stage, although benzene may be introduced into each alkylation stage, if desired. Since the alkylation is exothermic, the effluent is preferably cooled between stages in order to maintain similar temperature conditions in each stage.

In the manufacture of the alkylbenzenes, the overall benzene to alkyl group ratio is from about 2:1 to about 15:1, preferably from about 3:1 to about 10:1.

In another embodiment of the present invention, benzene is alkylated with an olefin, and effluent from the alkylator, in combination with recycle polyalkylbenzene, is introduced into a transalkylator.

In the transalkylator phenyl to alkyl group ratios are from about 2 to 50, preferably from about 4 to about 25.

In accordance with a further embodiment of the present invention, in producing cumene, dialkylbenzene, and a mixture of dialkyl and trialkylbenzenes are recovered from the alkylation effluent with the dialkylbenzene being recycled to the alkylator and the mixture of dialkylbenzenes and trialkylbenzenes being introduced into a transalkylator to produce additional cumene. In this embodiment, the dialkylbenzene introduced into the alkylator is essentially free of trialkylbenzene.

In accordance with yet another embodiment, there is provided a procedure for recovering materials from an alkylation effluent which includes a benzene column to recover unreacted benzene, a monoalkylbenzene column to recover alkylation product, and which may further include a polyalkylbenzene column to separate polyalkylbenzenes from heavier products. In accordance with one aspect, a portion of the bottoms fraction from the monoalkylbenzene column is passed to a stripper column to strip polyalkylbenzenes from said bottoms fraction and produce a remaining heavy material which includes diphenylalkane. The majority of the bottoms fraction from the monoalkylbenzene column is introduced into a transalkylator. As hereinafter described, the heavy material may be reacted to convert diphenylalkane to polyalkylbenzene, monoalkylbenzene and benzene. In another aspect, a major portion of the monoalkylbenzene column bottoms may be introduced into the transalkylator and a remaining portion directly into a diphenylalkane converter, as hereinafter described. In these aspects, the dialkylbenzene column is eliminated.

In accordance with yet another embodiment of the present invention, heavier materials produced in the process (diphenylalkane) are converted to polyalkylbenzene, monoalkylbenzene, and benzene by use of an alkylation catalyst, and in particular a zeolite catalyst. The bottoms from the polyalkylbenzene column (if employed) or a portion of the bottoms from the monoalkylbenzene column may be used as a feed to the diphenylalkane converter. The conversion of diphenylalkane may be accomplished in a separate reactor or the conversion may be accomplished in conjunction with recovery of various components; for example by use of a zeolite alkylation catalyst in an evaporator or stripper for recovering various components. The reaction effluent from the diphenylalkane conversion is subjected to a suitable recovery operation to separate and recover the various components of such effluent. Diphenylalkane conversion conditions are at a temperature from about 350° F. to about 800° F., preferably from about 450° F. to about 700° F., and for a residence time from about 5 minutes to about 80 minutes, preferably from about 10 minutes to about 60 minutes.

The preferred alkylbenzenes produced by the processes of this invention are cumene, also known as isopropylbenzene, and ethylbenzene. Cumene is produced from an alkylator feed of benzene and propylene, and ethylbenzene is produced from an alkylator feed of benzene and ethylene. Preferred distillation apparatuses used in connection with the processes of the present invention include a flasher column, a benzene column from which a portion of the benzene may be recycled to the alkylator, an ethylbenzene or cumene column, and/or a polyalkylbenzene column from which may be recovered di-isopropylbenzene, tri-isopropylbenzene, or polyethylbenzene. Heavy ends that are produced in these processes include diphenylpropane and diphenylethane. In the manufacture of cumene, the alkylator and/or transalkylator effluent may pass through a depropanizer prior to being distilled. In the manufacture of ethylbenzene, the effluent of the alkylator and/or transalkylator may pass through an aromatics recovery and/or flash column before entering the distillation apparatus.

The staging of the alkylation reaction by feeding olefin at the inlet of each stage of the alkylator enables excessive temperatures to be avoided and to reduce the overall benzene to olefin ratios while maintaining the ratio in each stage at a value high enough to reduce the temperature rise in each stage to improve thereby selectivity and lengthen catalyst life. Lower temperatures enable the maintenance of the liquid phase in the presence of the zeolite catalyst and will prolong the time before the zeolite catalyst must be regenerated. The staging also helps increase yield of the desired alkylbenzene product and reduces the benzene recycle rate.

Thus in a preferred aspect, the number of stages and the amount of olefin introduced in each stage are coordinated to limit the temperature rise in each stage as hereinabove described. The higher the benzene to olefin ratio in each stage the lower the temperature rise in each stage.

Alkylation conditions for each adiabatic stage of the alkylation reaction area zone may be as follows:

TABLE 1

| Broad Range | | Preferred Range |
| --- | --- | --- |
| Outlet Temperature, °F. | 150–900 | 200–600 |
| Pressure, psig | 150–2,000 | 250–1,000 |
| Total LHSV | 2–1,000 | 4–100 |

In the manufacture of cumene, the overall benzene to propylene ratio, including isopropyl groups, is from about 2:1 to about 10:1, preferably at least about 3:1. In the manufacture of ethylbenzene, the overall benzene to ethylene group mole ratio is from about 2:1 to about 15:1, preferably from about 3:1 to 10:1.

The invention will now be described with respect to the drawings, wherein:

FIG. 2 is a schematic diagram showing the use of an "integral" transalkylator in accordance with an embodiment of the present invention;

FIG. 3 is a diagram of a di-isopropylbenzene column wherein a portion of the di-isopropylbenzene is passed to an alkylator;

FIG. 4 is a diagram of a stripper of cumene column bottoms;

FIG. 5 is a diagram of a diphenyl propane converter which converts a feed of cumene column bottoms;

FIG. 7 is a schematic diagram of the use of an "integral" transalkylator used in the manufacture of ethylbenzene in accordance with the present invention;

FIG. 8 is a diagram of a stripper of ethylbenzene column bottoms; and

FIG. 9 is a diagram of a diphenylethane converter which converts ethylbenzene column bottoms or a stripped ethylbenzene column bottoms purge stream.

Figure 1:
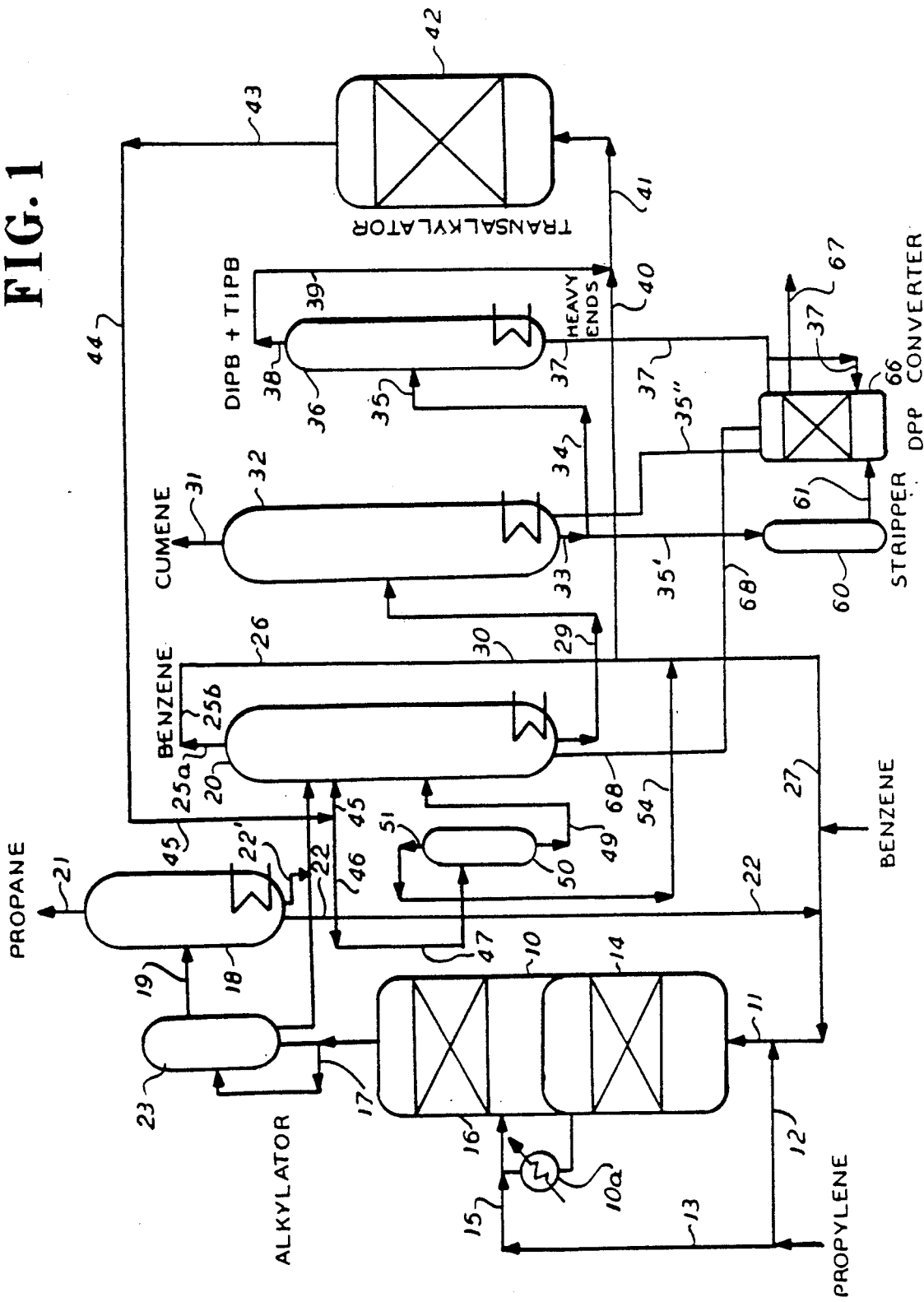
FIG. 1 is a schematic diagram of an embodiment of an apparatus for the manufacture of cumene in accordance with the present invention.

Referring now to the drawings, in the manufacture of cumene, a mixture of fresh and recycle benzene and fresh propylene is fed into an inlet of alkylator 10 through line 11 as shown in FIG. 1. Propylene from line 12 joins the benzene in line 11 before entering alkylator 10. The alkylator preferably has from 2 to 4 stages. For purposes of illustration, alkylator 10 has two stages, 14 and 16. In these stages 14 and 16 is contained an alkylation catalyst. Preferred examples of catalysts which may be used in this invention are zeolite X, zeolite Y, zeolite L, zeolite Beta, ZSM-5, Omega crystal zeolites, mordenite, chabazite, etc. In addition to being fed into stage 14 of alkylator 10 through line 11, fresh propylene is also fed into stage 16 of alkylator 10 via lines 13 and 15. The reaction conditions are the same as those described in Table 1. Substantially all of the propylene fed into alkylator 10 through lines 11 and 15 is reacted with the benzene in stages 14 and 16 respectively.

In each of stages 14 and 16, it is preferred that an adiabatic reaction takes place. It is also preferred that the temperature rise in each of the stages 14 and 16 of alkylator 10 is no more than 100° F., preferably no more than 75° F. The feed propylene concentration may be as low as 50 vol.%, but the presence of other olefins could cause the formation of unwanted alkylbenzene products which could lower cumene purity. A small degree of transalkylation may also occur in stages 14 and 16 of alkylator 10. All of the benzene is introduced into stage 14 and essentially all of the propylene introduced into stage 14 is reacted with the benzene prior to passage of the effluent from stage 14 into stage 16. The effluent from stage 14 prior to combination with propylene in line 13 is cooled in heat exchanger 10A. As hereinabove described, in a preferred embodiment the cooling is effected to achieve temperature conditions in stage 16 similar to those for stage 14.

The effluent from the second stage 16 of alkylator 10 enters a distillation system which recovers propane, recycle benzene, cumene product, di-isopropylbenzene, tri-isopropylbenzene, and so-called heavy ends bottoms which contains diphenylpropane. The effluent from alkylator 10 passes through line 17 to flasher 23. Benzene and heavier aromatics pass through line 24 to benzene column 20. Propane and some benzene are withdrawn from flasher 23 as overhead and are passed through line 19 to depropanizer 18. Propane is distilled off through line 21, and the benzene is recycled through lines 22 and 27 to alkylator 10. Alternatively, the effluent from alkylator 10 is passed directly to depropanizer 18. Propane is then distilled off through line 21, and benzene and heavier aromatics recovered as bottoms are passed to benzene column 20 through line 22'. Benzene overhead withdrawn from benzene column 20 through line 25a passes through lines 25b, 26, and 27 as recycle benzene to alkylator 10. The bottoms effluent from benzene column 20 passes through lines 28, 29, and 30 to cumene column 32 wherein cumene product is distilled off through line 31. The bottoms from cumene column 32 passes through lines 33, 34 and 35 to di-isopropylbenzene or DIPB column 36, to separate di- and tri-propylbenzenes as overhead. So-called heavy ends, in particular di-phenylpropane, is withdrawn from DIPB column 36 through line 37.

When a portion of the cumene column bottoms is not sent to diphenyl propane converter 66, the DIPB column 36 is used. Cumene column bottoms are introduced into the DIPB column 36 through line 35. The overhead is introduced to transalkylator 42 as described below. Heavy ends are withdrawn through line 37 and passed to diphenyl propane converter 66. Unconverted heavy ends are withdrawn from diphenyl propane converter 66 through line 67, and lighter aromatics are withdrawn through line 68 to be returned to the benzene column 20 or to the DIPB column 36 for further distillation and/or processing. Catalytic conversion conditions for the heavy ends introduced into the diphenyl propane converter 66 through line 37 are the same as those when the bottoms from a cumene column are introduced. The diphenyl propane converter may also function as an evaporator.

The overhead of the DIPB column, 36 containing principally di-isopropylbenzene (DIPB) and tri-isopropylbenzene, (TIPB) is passed through lines 38, 39 and 41 to transalkylator 42. Also being transported to transalkylator 42 is an excess of recycle benzene in line 40 which has been recovered from benzene column 20. This recycle benzene is diverted from line 26 to line 40 to be mixed with the DIPB and TIPB at line 41. The benzene, DIPB, and TIPB then enter transalkylator 42. Transalkylator 42 may contain the same type of catalyst contained in alkylator 10.

Transalkylation conditions may be as follows:

|  | Broad Range | Preferred Range |
| --- | --- | --- |
| Temperature °F. | 150–900 | 300–550 |
| Pressure, psig | 150–2,000 | 250–1,000 |
| Total LHSV | 1–1,000 | 2–100 |
| Phenyl to Alkyl Group Ratio | 2–50 | 4–25 |

The reactions which take place in transalkylator 42 are equilibrium-limited. The transalkylator 42 operates isothermally because there is almost no heat of reaction. The reactions which take place in transalkylator 42 are are follows:

| Benzene + DIPB | 2 cumene |
| --- | --- |
| Cumene + TIPB | 2 DIPB |

An excess of benzene is required to preserve catalyst activity and to move the equilibrium of these reactions toward cumene, thus obtaining higher DIPB and TIPB conversions.

The transalkylator effluent is passed through lines 43, 44, and 45 to benzene column 20 in that the effluent does not contain propane. The effluent is then distilled in benzene column 20, cumene column 32, and DIPB column 36 as described above.

The transalkylator effluent can be diverted from line 45 and passed through lines 46, 47 and 48 to flasher 50. The flasher 50 flashes benzene, which passes through lines 51, 52, 53 and 54 to line 26 as recycle, while the remainder of the flasher effluent is passed through line 49 to benzene column 20.

Another embodiment of the present invention involves the use of an "integral" transalkylator as shown in FIG. 2. In this process fresh feed and recycle benzene and fresh feed propylene are introduced into the alkylator 10 in the same method as given in the description of FIG. 1. In this embodiment, however, the effluent from alkylator 10 is passed through line 17 to transalkylator 42 instead of to a distillation apparatus beginning with a flasher and a depropanizer. Transalkylation takes place in transalkylator 42 in the presence of an alkylation catalyst. The effluent from transalkylator 42 then passes to a distillation and recovery system (for example as described with reference to FIG. 1) to recover cumene, benzene, propane and DIPB and TIPB and heavy ends. Propane is recovered through line 21, benzene through line 25, cumene through line 31, and heavy ends through line 37. DIPB and TIPB are withdrawn through lines 38, 39 and 41'. Line 41' transports the DIPB and TIPB to line 17, where the DIPB and TIPB is combined with the effluent from alkylator 10. In this process, no recycle benzene is mixed with the DIPB and TIPB introduced into the transalkylator 42. The result is a reduction in benzene recycle.

In a modification of the processes shown in FIGS. 1 and 2, the DIPB column (FIG. 3) is operated to recover di-isopropylbenzene as overhead (line 58) a mixture of di- and tri-isopropylbenzene as a side stream (line 38). Cumene column bottoms are introduced into the DIPB column 36 through line 35. Heavy ends are withdrawn through line 37. The DIPB overhead is withdrawn from DIPB column 36 through line 58 for direct introduction into alkylator 10. In this way, a portion of the DIPB is transported directly to the alkylator 10 as opposed to being transported to a transalkylator. The rest of the DIPB and the TIPB are withdrawn from DIPB column 36 through line 38, for introduction into transalkylator 42 as described above. In this process, the benzene recycle is increased over that of the "integral" transalkylator process shown in FIG. 2, but yield loss is reduced and catalyst activity is maintained at a desirable rate.

Alternative processes for recovering and converting cumene column bottoms are shown in FIGS. 4 and 5. In FIG. 4, a major portion of the cumene column bottoms in line 35' is passed through lines 62 and 64 directly to transalkylator 42. A remaining stream of cumene column bottoms is passed through line 35' to stripper 60 to strip polyalkylbenzenes from heavy ends. Heavy ends are withdrawn through line 61. The overhead from the stripper 60 is withdrawn through lines 63, and 64 and transported to transalkylator 42. Although a stripper is shown, an evaporator or other equipment may be used. In this embodiment there is no DIPB column.

In FIG. 5, a portion of the cumene column bottoms in line 35 is diverted to transalkylator 42 through lines 62 and 64. Another portion of the cumene column bottoms is transported through line 35'' to diphenylpropane converter 66. In this embodiment, there is no DIPB column. Contained within diphenyl propane converter 66 is a zeolite alkylation catalyst which is able to convert a substantial portion of the cumene column bottoms from line 35'' into lighter aromatics such as benzene, DIPB, and TIPB. Unconverted heavy ends are withdrawn through line 67, while the lighter aromatics are withdrawn through line 68 to be returned ultimately to the benzene column 20. Catalytic conversion conditions in diphenyl propane converter 66 are at a temperature from about 350° F. to about 800° F., preferably from about 450° F. to about 700° F., and a residence time from about 5 minutes to about 80 minutes, preferably from about 10 minutes to about 60 minutes. The diphenyl propane converter, in one embodiment, may function as an evaporator.

Figure 6:
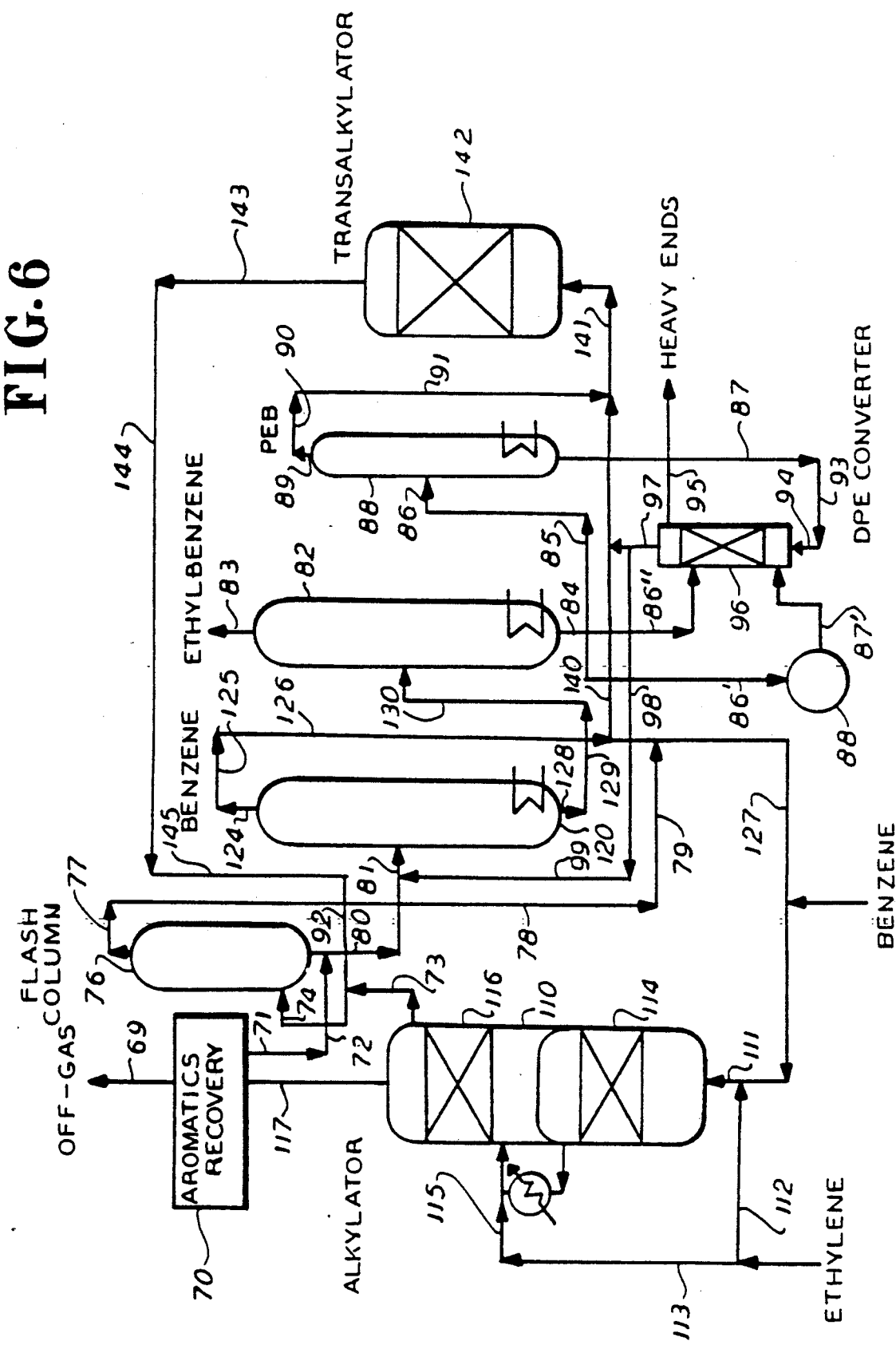
FIG. 6 is a schematic diagram of an embodiment of an apparatus for the manufacture of ethylbenzene in accordance with the present invention.

In FIG. 6 there is shown a process of the present invention which is employed in the manufacture of ethylbenzene. Fresh and recycle benzene enter alkylator 110 through line 111. The alkylator 110 may have from one to four stages. For purposes of illustration, alkylator 110 has two stages 114 and 116. Fresh ethylene passes through lines 112 and 111, to enter stage 114 of alkylator 110, as well as passing through lines 113 and 115 to enter stage 116 of alkylator 110. In each of stages 114, 116 is an alkylation catalyst. The reacting mixture temperature rises across each stage no more than 100° F., preferably no more than 75° F.; however, cooling is preferably effected between stages so that the maximum temperature at the exit of each stage is approximately equal. The ethylene reacts substantially completely with the benzene at each stage of alkylator 110. Staging of the reaction with respect to ethylene addition and cooling improves yield and helps to prolong the life of the catalyst. The overall benzene to olefin ratios are reduced while the benzene to olefin ratio in each stage is maintained high enough to reduce the temperature rise in each stage to improve selectivity and lengthen catalyst life.

Feed ethylene concentration may be as low as about 30%, however, the presence of higher olefins may cause the production of by products such as cumene which may be difficult to separate from the desired ethylbenzene product.

Inert gases such as methane, and ethane, as well as some aromatics, leave alkylator 110 through line 117 to aromatics recovery zone 70. The inert gases are withdrawn through line 69. Aromatics are withdrawn through lines 71, 72, 80 and 81 and passed to benzene column 120, wherein these aromatics will be distilled.

A liquid phase is withdrawn from alkylator 110 through lines 73 and 74 to benzene column 120 or to an optional flash column 76. Flash column 76, when used, vaporizes much of the benzene. The bottoms of the flash column 76 is withdrawn through lines 80 and 81 to benzene column 120, while the overhead travels through lines 75, 77, 78 and 79 to line 126, where this overhead is mixed with distilled benzene to form a recycle benzene stream in lines 126 and 127. Line 127 carries the recycle benzene to line 111 which leads to alkylator 110.

Distilled benzene is withdrawn through lines 124, 125 and 126 and then is transported to line 127 as a recycle benzene stream. The bottoms of the benzene column 120 is withdrawn through line 128 and transported through lines 129 and 130 to ethylbenzene column 82. Ethylbenzene is withdrawn from ethylbenzene column 82 through line 83, while the bottoms is withdrawn through line 84 and transported through lines 85 and 86 to polyethylbenzene (PEB) column 88. The PEB is withdrawn from PEB column 88 through line 89, and transported through lines 90 and 91. The PEB then joins with a benzene stream from line 140, said stream having been diverted from line 126, and travels through line 141 to transalkylator 142. In transalkylator 142, the PEB and benzene are reacted in the presence of a catalyst to form ethylbenzene. The transalkylator 142 operates isothermally because there is essentially no heat of reaction. The reactions are also equilibrium-limited. The equilibrium reactions are as follows:

Benzene + diethylbenzene 2 ethylbenzene

Ethylbenzene + triethylbenzene 2 diethylbenzene

An excess of benzene is required to preserve catalyst activity and to move the equilibrium toward ethylbenzene, thus obtaining high conversions of diethylbenzene and triethylbenzene. The transalkylation effluent then travels through line 143, 144, 145 and 92 and then joins with alkylator effluent in line 74 and travels to the flash column 76, thus accomplishing a recycle to the distillation train. Alternatively, the transalkylator effluent may be processed separately through the benzene column 120. Also, some diethylbenzene may be fed to alkylator 110, where transalkylation may take place to some extent in either or both of stages 114 and 116.

The PEB column bottoms, which contain tetraethylbenzene, diphenylethane, and other high-boiling aromatics, are withdrawn from PEB column 88 through line 87, travel through lines 93 and 94 to DPE (diphenylethane) converter 96 wherein the PEB column bottoms is converted to benzene, ethylbenzene and diethylbenzene, as well as a small amount of high boiling aromatics in the presence of a zeolite catalyst. Catalytic conversion conditions for the DPE converter 96 are temperatures of about 350° F. to about 800° F., preferably from about 450° F. to about 700° F., and residence times from about 5 minutes to about 80 minutes, preferably from about 10 minutes to about 60 minutes. The heavy ends are withdrawn from DPE converter 96 through line 95, while the lighter aromatics are withdrawn through line 97. A portion of the lighter aromatics is passed through lines 140, 141 to transalkylator 142. Another portion is passed through lines 98, 99 and 81 to benzene column 120.

In an alternative embodiment shown in FIG. 7, the overhead from PEB column 88 is withdrawn through lines 89, 90, 91 and 141' to line 117 wherein the PEB column overhead is mixed with the effluent from alkylator 110 in line 117 before travelling to a so-called "integral" transalkylator 142. Transalkylation takes place in the presence of a catalyst. The effluent from transalkylator 142 is then withdrawn through lines 100, 101 and 102 and transported to the distillation portion of the apparatus, beginning with benzene column 120. The use of an "integral" transalkylator reduces the amount of benzene recycle.

Alternative embodiments for converting the ethylbenzene column bottoms are shown in FIGS. 8 and 9. In FIG. 8, a purge stream of the ethylbenzene column bottoms is passed through line 86' to stripper 88' in order to remove heavy ends, while the major portion is diverted through line 103, which carries most of the ethylbenzene column bottoms to line 141, where the ethylbenzene column bottoms are passed to transalkylator 142. The heavy ends recovered from the stripper is introduced into the diphenylalkane converter through line 87'.

In FIG. 9, the ethylbenzene column bottoms are fed directly through line 86" to DPE converter 96, or a stripped ethylbenzene column bottoms purge stream which was fed to stripper 88' is fed to DPE converter 96 through line 87'. In cases where the DPE converter is fed with ethylbenzene column bottoms directly or fed with an ethylbenzene column bottoms purge stream, the DPE converter 96 functions as an evaporator. When the DPE converter is fed with ethylbenzene column bottoms directly or with a purge stream, the PEB column is eliminated. Conversion takes place in the presence of a zeolite catalyst at the DPE conversion conditions mentioned above. Heavy ends are withdrawn through line 95, and the overhead light aromatics effluent is withdrawn through line 97 for transport to transalkylator 142 or benzene column 120.

It is to be understood, however, that the scope of the invention is not to be limited to the specific embodiments described above. Variations of different aspects of the processes of this invention may be made and still be within the scope of the accompanying claims.

What is claimed is:

1. A process for the liquid phase alkylation of benzene in the presence of a zeolite alkylation catalyst, comprising:
introducing benzene into an alkylator having only two reaction stages, each stage containing a zeolite alkylation catalyst, with essentially all of the benzene requirements being introduced into the first stage, and introducing a feed of fresh olefin into each of said two stages of said alkylator, essentially completely reacting the olefin with said benzene in each reaction stage of said alkylator, said alkylation being effected in said two stages at an overall benzene to olefin ratio of about 2:1 to about 15:1, and recovering net product from the second stage, whereby essentially all of the olefin requirements for the alkylation are introduced into only two stages.

2. The process of claim 1, wherein each of said two reaction stages is adiabatic.

3. The process of claim 2 wherein the alkylation conditions in each of said two reaction stages are at temperatures from about 150° F. to about 900° F., and at a pressure from about 150 psig to about 2,000 psig.

4. The process of claim 3 wherein the alkylation conditions in each of said two reaction stages are at temperatures from about 200° F. to about 600° F., and a pressure from about 250 psig to about 1,000 psig.

5. The process of claim 1 wherein the temperature conditions of each stage of said alkylator remain essentially the same.

6. The process of claim 1 wherein the temperature rise in each stage of said alkylator does not exceed about 100° F.

7. The process of claim 6 wherein said temperature rise in each stage of said alkylator does not exceed about 75° F.

8. The process of claim 6 wherein cooling occurs between each of said stages of said alkylator.

9. The process of claim 1 wherein said benzene and said olefin are reacted in said alkylator to produce an alkylation effluent containing mono-and polyalkylbenzene, and said process further comprises:
   directly introducing alkylation effluent, without prior separation of products therefrom, and recycle polyalkylbenzene into a transalkylation zone to convert polyalklybenzene to monoalkylbenzene and produce a transalkylation effluent containing monoalkyl and polyalkylbenzene; and
   recovering monoalkylbenzene product and recycle polyalkylbenzene from the transalkylation effluent.

10. The process of claim 1 wherein said olefin is propylene, and said benzene is alkylated with said propylene in said alkylator to produce an alkylation effluent containing cumene, diisopropylbenzene, and triisopropylbenzene, and said process further comprises:
   separating and recovering from the alkylation effluent diisopropylbenzene and a mixture of diisopropylbenzene and triisopropylbenzene; introducing the diisopropylbenzene into the alkylator; and
   transalkylating said mixture to produce cumene.

11. The process of claim 1 wherein said benzene and said olefin are reacted in said alkylator to produce an alkylation effluent containing monoalkylbenzene, polyalkylbenzenes, and diphenylalkanes, and said process further comprises:
   passing said effluent through a separation and recovery zone comprising a monoalkylbenzene column to separate monoalkylbenzene from a bottoms fraction containing polyalkylbenzenes and diphenylalkane;
   passing a first portion of said bottom fraction to a transalkylator;
   stripping a second portion of said bottoms to separate polyalkylbenzenes from heavier components comprising diphenylalkanes; and
   passing separated polyalkylbenzenes to a transalkylator.

12. The process of claim 1 wherein said benzene and said olefin are reacted in said alkylator to produce an effluent containing a monoalkylbenzene product and a diphenylalkane by-product, and wherein the process further comprises:
   contacting said diphenylalkane by-product with a zeolite catalyst to produce an effluent containing benzene and alkylbenzenes.

13. The process of claim 12 wherein said diphenylalkane by-product is contained in a portion of a bottom stream recovered from a distillation column for recovering monoalkylbenzene.

14. The process of claim 12 wherein said diphenylalkane by-product is contained in a portion of a bottoms stream recovered from a distillation column for recovering polyalkylbenzenes.

15. The process of claim 12 wherein said at least one diphenylalkane is selected from the group consisting of diphenylethane and diphenylpropane.

16. The process of claim 12 wherein said diphenylalkane is contacted with the catalyst at temperatures from about 350° F. to about 800° F.

17. The process of claim 16 wherein said temperature is from about 450° F. to about 700° F.

18. The process of claim 11 wherein said heavier components are contacted with a zeolite catalyst at a temperature of from about 350° F. to 800° F. to convert diphenylalkane to benzene and alkylbenzenes.

19. The process of claim 12 wherein said diphenylalkane by-product is free of di-isopropylbenzenes and tri-isopropylbenzenes.

* * * * *